US012714444B2

(12) United States Patent
Leveille et al.

(10) Patent No.: US 12,714,444 B2
(45) Date of Patent: Aug. 25, 2026

(54) KNEE ARTHROPLASTY INSTRUMENT WITH SENSING CAPABILITY

(71) Applicant: Orthosoft ULC, Montreal (CA)

(72) Inventors: Catherine Leveille, Longueuil (CA); Jerome Casaubon, Montreal (CA)

(73) Assignee: Orthosoft ULC, Montreal (CA)

( * ) Notice: Subject to any disclaimer, the term of this patent is extended or adjusted under 35 U.S.C. 154(b) by 187 days.

(21) Appl. No.: 18/603,495

(22) Filed: Mar. 13, 2024

(65) Prior Publication Data

US 2024/0307075 A1 Sep. 19, 2024

Related U.S. Application Data

(60) Provisional application No. 63/452,285, filed on Mar. 15, 2023.

(51) Int. Cl.
*A61B 17/17* (2006.01)
*A61F 2/38* (2006.01)

(52) U.S. Cl.
CPC ........ *A61B 17/1764* (2013.01); *A61F 2/3859* (2013.01); *A61F 2/389* (2013.01); *A61F 2250/0012* (2013.01); *A61F 2250/0096* (2013.01)

(58) Field of Classification Search
CPC .......... A61B 17/025; A61B 2017/0268; A61B 2090/066; A61B 34/30; A61B 34/25; A61F 2/461; A61F 2002/4667; A61F 2002/4668
See application file for complete search history.

(56) References Cited

U.S. PATENT DOCUMENTS

| | | | | |
|---|---|---|---|---|
| 6,022,377 | A | 2/2000 | Nuelle et al. | |
| 7,156,853 | B2 | 1/2007 | Muratsu | |
| 10,166,034 | B2 | 1/2019 | Claypool et al. | |
| 10,952,755 | B2 | 3/2021 | Toler et al. | |
| 11,602,443 | B1 | 3/2023 | Cole et al. | |
| 2017/0360512 | A1* | 12/2017 | Couture | A61B 34/10 |
| 2019/0290452 | A1 | 9/2019 | Trabish et al. | |
| 2022/0202463 | A1 | 6/2022 | Angibaud et al. | |
| 2023/0172600 | A1* | 6/2023 | Dumpe | A61B 34/20 606/90 |

FOREIGN PATENT DOCUMENTS

CN 114569297 6/2022

OTHER PUBLICATIONS

"European Application Serial No. 24163642.2, Communication Pursuant to Article 94(3) EPC mailed Nov. 17, 2025", 7 pgs.

(Continued)

*Primary Examiner* — Samuel S Hanna
(74) *Attorney, Agent, or Firm* — SCHWEGMAN LUNDBG & WOESSNER, P.A.

(57) ABSTRACT

A knee arthroplasty instrument may include a tensioning instrument and at least a first sensor. The tensioning instrument can optionally include a tibial component configured to engage the tibia and a femoral component configured to engage the femur. The femoral component can be movably coupled to the tibial component to place the knee joint in tension by separating the tibia and the femur. The first sensor can be coupled to the tensioning instrument and can be configured to collect first data regarding a torque of the tensioning instrument when separating the tibia and the femur.

15 Claims, 7 Drawing Sheets

(56) References Cited

OTHER PUBLICATIONS

"European Application Serial No. 24163642.2, Extended European Search Report mailed Jul. 30, 2024", 9 pgs.
"European Application Serial No. 24163642.2, Response filed Feb. 28, 2025 to Extended European Search Report mailed Jul. 30, 2024", 12 pgs.
"European Application Serial No. 24163642.2, Response filed Feb. 24, 2026 to Communication Pursuant to Article 943 EPC mailed Nov. 17, 2025", W English Claims, 10 pgs.

* cited by examiner

KNEE ARTHROPLASTY INSTRUMENT WITH SENSING CAPABILITY

CLAIM OF PRIORITY

This application claims the benefit of U.S. Provisional Patent Application Ser. No. 63/452,285, filed on Mar. 15, 2023, the benefit of priority of which is claimed hereby, and which is incorporated by reference herein in its entirety.

FIELD

The present application relates to a surgical knee arthroplasty and to an instrument and a robotic surgical system used in the knee arthroplasty.

BACKGROUND

A knee replacement procedure (e.g., knee arthroplasty) is used to repair or replace damaged bone or damaged tissue in a patient knee joint. A total knee arthroplasty (TKA) includes repairing or replacing damaged or diseased articular surfaces of the tibia and femur. The arthroplasty procedure may include cutting (e.g., resecting) articular surfaces of the tibia and femur and replacing each articular surface with a prosthesis (e.g., implant).

Many factors influence joint motion after the arthroplasty procedure. The size and shape of each implant will impact joint motion. Additionally, the location and orientation of each implant, which is determined by the location and orientation of the corresponding bone resections, will impact joint motion. The tension or laxity of the surrounding soft tissue will also impact joint motion. For example, if the surrounding collateral ligaments are too tense, joint motion may be limited, but if the surrounding collateral ligaments are too lax, improper femoral rotation or femoral lift-off may occur. Also, the soft tissue balance around the joint will impact joint motion. Determining tension or laxity is subjective and subject to errors.

DETAILED DESCRIPTION

Figure 1:
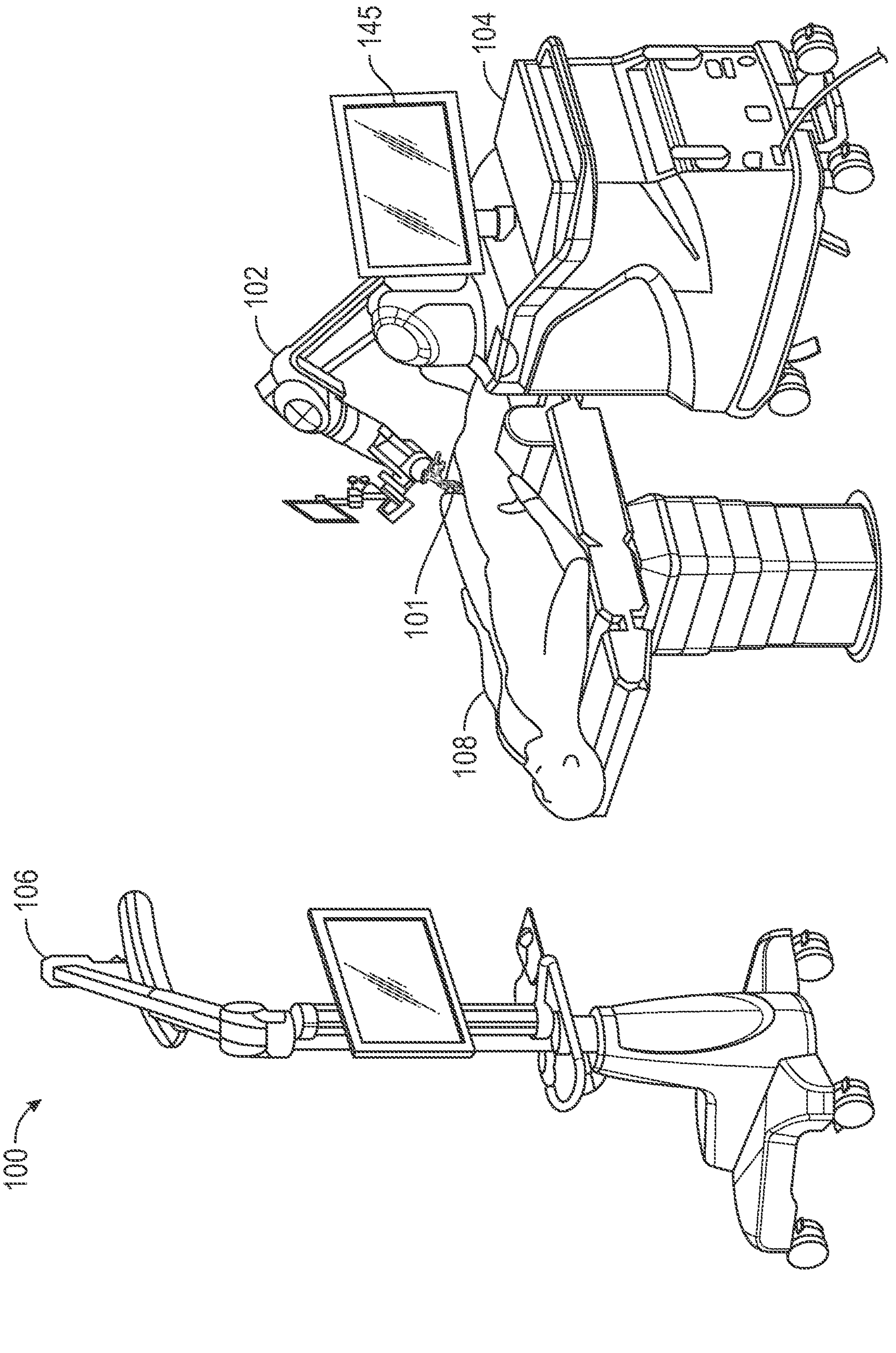
FIG. 1 is a schematic view of a robotic surgical system including a robotic surgical device (e.g., a robot or a robotic arm) and a computer (e.g., a device having a processing circuitry) in accordance with at least one example of this disclosure.

The present disclosure describes technical solutions to various technical problems facing knee arthroplasty procedures. The present inventors propose adding one or more sensors to a tensioning instrument to quantify tension or laxity of the surrounding soft tissue as data and provide one or more other optional sensors to collect other useful quantifiable data. The tension or laxity of the knee joint is dictated by surrounding soft tissue. This tension or laxity has formerly been subjectively determined by a surgeon. Quantifiable data can be used to make a more precise and accurate determination of tension or laxity of the knee joint, thereby allowing the surgeon to make more accurate determination of a proper gap between the femur and the tibia, a more accurate selection of implant components, a more accurate selection and positioning of femoral joint resection instruments, etc. A more simplified and more precise knee replacement procedure will result from use of the tensioning instrument proposed by the present inventors.

The present disclosure provides the tensioning instrument is used during a TKA procedure. The tensioning instrument can separate the patient's tibia and femur, in both extension and flexion, to place the soft tissue (and hence knee joint) in tension and to measure a gap and an angle between the femur and the tibia. The tensioning instrument can be used before resecting or otherwise manipulating the patient's femur to plan aspects of the TKA procedure. Portions of the tensioning instrument can be constructed in the manner discussed in U.S. Pat. Nos. 10,952,755, 10,166,034, and 7,156,853, the entire disclosure of each of which is incorporated herein by reference. Some aspects of the tensioning instrument can be similar to those of the Zimmer FuZion™ Device, which is commercially manufactured by Zimmer Biomet Inc. of Warsaw, IN. However, the present inventors propose the addition of the one or more sensors to the tensioning instrument to quantify tension or laxity of the knee joint as data. The tensioning instrument can additionally include other sensors to provide other useful quantifiable data. Such data can be utilized by a robotic surgical system, a computer aided surgical (CAS) system and/or for predictive analytics, to generate models and for other purposes. Use of the robotic surgical systems and/or CAS systems and methods may improve surgical precision, for example, in accessing tension or laxity of the knee joint, in generating a plan in response to such tension or laxity of the knee joint (e.g., in making recommendation(s) to the surgeon) and in improving selection, size and positioning of implant(s) and/or resection(s) in response to the tension or laxity of the knee joint. The example of FIG. 1 describes the tensioning instrument used in combination with a robotic surgical system. However, it is recognized that the data gathered by the one or more sensors of the tensioning instrument can be used with other CAS systems or can be used by electronic or mobile devices.

FIG. 1 illustrates a robotic surgical system 100 including a robotic surgical device 102 (sometimes referred to herein a robotic surgical arm) and a computing device 104 (e.g., a device having processing circuitry) in accordance with at least one example of this disclosure. In an example, the robotic surgical device 102 and the computing device 104 may be coupled, such as communicatively coupled or physically connected.

The computing device 104 can include at least memory, a processing unit, and user input devices, as will be described herein. The computing device 104 can also include human interface device 145 for providing models and images for a surgeon to be used during surgery. The computing device 104 is illustrated as a separate standalone system, but in some examples computing device 104 can be integrated into robotic surgical system 100. Human interface device 145 can provide models and/or images, including but not limited to three-dimensional images of bones, joints, virtual implants, landmarks, and the like as further discussed herein. The human interface device 145 can include associated input mechanisms, such as a touch screen, wearable, mixed reality device, mouse, display, foot pedals, or other input and/or output devices compatible with a surgical environment.

The robotic surgical system 100 is for operation on surgical area of a patient 108 in accordance with at least one example of the present disclosure. Surgical area in one example can include a joint and, in another example, can be a knee joint. Surgical area can include any surgical area of patient, including but not limited to the shoulder, head, elbow, thumb, spine, and the like. However, aspects of the present application are directed to a knee arthroplasty procedure. The robotic surgical system 100 can also include one or more robotic devices 102. As illustrated, robotic surgical system 100 can utilize only a single robotic arm. Robotic surgical device 102 can be a 6 degree-of-freedom (DOF) robot arm, such as the ROSA® robot from Medtech, a Zimmer Biomet Holdings, Inc. company. In some examples, robotic surgical device 102 is cooperatively controlled with surgeon input on the end effector or surgical instrument. In other examples, robotic surgical device 102 can operate autonomously. While not illustrated in FIG. 1, one or more positionable surgical support arms can be incorporated into robotic surgical system 100 to assist in positioning and stabilizing instruments or anatomy during various procedures.

While not shown in FIG. 1, the robotic surgical device 102 can rotate axially and radially and can receive a surgical instrument, or end effector, at a distal end. The surgical instrument can be any surgical instrument adapted for use by the robotic system, including, for example, a guide tube, a holder device, a gripping device such as a pincer grip, a burring device, a reaming device, cut guide, an impactor device such as a humeral head impactor, a pointer, a probe or the like. The surgical instrument can be positionable by robotic surgical device 102, which can include multiple robotic joints, that allow the surgical instrument to be positioned at any desired location adjacent or within a given surgical area.

The robotic surgical system 100 can be in electronic communication with one or more sensors of a tensioning instrument 101 as further discussed herein. Data gathered by the one or more sensors of the tensioning instrument 101 during operation within the knee joint can be received by the robotic surgical system 100 via wired or wireless connection for analysis by the computing device 104.

The robotic surgical device 102 can be separately registered to the coordinate system of the robotic surgical system 100, such via use of a navigation system 106. Fiducial markers can additionally be separately registered to the coordinate system of the robotic surgical system 100 via engagement with a probe having a tracking element attached thereto. As such, some or all of the components of the robotic surgical system 100 can be individually registered to the coordinate system and, if desired, movement of such components can be continuously or intermittently tracked with the navigation system 106.

In terms of surgical planning or recommendation, an operator may refer to and/or make selections using the human interface device 145 (such as a display). Such display can indicate various items such as a torque on the tensioning instrument, a tension on the tensioning instrument as a result of separating the knee joint (this can be derived from the torque for example), a position of a femoral component of the tensioning instrument relative to a tibial component (equivalent to an extension gap or flexion gap between the femur and the tibia), a position of one or more resections such as to the femur, a position, size and/or orientation of a 3D model of an implant relative to the bone, etc. In another example, recommendations such as an amount of torque for the tensioning instrument, a desired tension of the knee joint, a desired position of the femur relative to the tibia, a location or orientation of resection(s) to the femur, a size of the implant(s) may be suggested or automatically generated (e.g., using machine learning). Planning may include alerts such as for advice, warnings, reminders, or the like as further discussed herein. Models and other data described with respect to the patient anatomy need not be actually rendered or displayed. Instead, the models may be used by the robotic surgical system 100 to perform portions of a procedure. For example, data from the one or more sensors of the tensioning instrument may be stored in memory. The robotic surgical system 100 may retrieve the data stored in the memory and used when performing a portion of the procedure such as making resection to the femur, providing advice or implanting a femoral implant, for example. In yet further embodiments, display may be performed on a mixed reality device such as eyewear worn by a surgeon performing the procedure.

In an example, the robotic surgical device 102 may be used to cut the bone, for example using a reference guide developed from data including the data generated by the one or more sensors of the tensioning instrument. The robotic surgical device 102 may autonomously perform the cut. Several optical navigation devices (e.g., trackers) may be used, for example one on each of a femur, tibia, the robotic surgical device 102, etc. From the tracking information gathered by the optical navigation system 106, used to track each of the optical navigation devices, the robotic surgical device 102 may be guided to perform the cut such as to the distal femur. It is further contemplated in some examples that the robotic surgical device 102 (or another CAS system) could be used to autonomously operate a tensioning instrument similar to the tensioning instrument that is disclosed herein. Such operation could be achieved by the use of the one or more sensors disclosed in combination with one or more actuators (e.g., motors, pneumatics, etc.) that can be used to apply torsion to the tensioning instrument to separate the femur from the tibia as further described herein.

Various models and related software have been developed that can be utilized by the robotic surgical device 102, another CAS system or electronic device. These include Mymobility® a commercially developed orthopedic care management system operated by Zimmer Biomet, Inc. to perform data analytics and other analysis to help patients and patient care providers deliver a personalized surgical experience. Additionally, mean bone models and related software have been developed. Such mean bone models may be determined based on, or according to, data stored in an anatomic database. For example, ZiBRA™ Analytical Modeling System is one such an anatomic database from Zimmer Biomet, Inc. ZiBRA™ is a database used to collect and analyze anatomic data. The operating thesis for ZiBRA™ is that when used to design orthopedic components they will conform better to the anatomy and provide increased clinical options. The ZiBRA™ software application enables: statistical shape analysis, virtual surgery, component placement optimization, and implant fit assessment.

The computing device 104 may use one or more of the models and software described above. These modeling systems and software can be stored in a planning subsystem of the robotic surgical system 100 or can otherwise be in communication therewith. Patient demographics (patient height, patient weight, patient gender, etc.) and/or other data can be used to select an appropriate model from the modeling system. Optionally, preoperative imaging of the patient may aid in the selection of the model.

The computing device 104 can also be configured based upon patient anatomy (including the tension or laxity of the surrounding soft tissue as measured with the one or more sensors of the tensioning instrument) and/or demographics to perform alteration, modification or deformation of the selected model. Such modification can be based upon sensed data, demographics, soft tissue or other information. Patient demographics can include patient height, patient weight, patient gender, patient age, patient knee state or the like. This modification allows the computing device 104 to be predictive as to what tensioning, gap(s), cuts and/or implants should be utilized during the surgical procedure. From the predicted anatomy and/or data, an updated model may be determined or kinematic information may be determined.

In some TKA procedures, there is no uncomplicated way to size the femur if a gap balancing technique is utilized. This is because traditional femoral sizers measure the anterior to posterior distance referenced from the posterior condyles to the anterior cortex. However, if an amount (thickness) of a posterior resection of the posterior condyles is not the same as a thickness of a femoral implant, the anterior to posterior distance measured by the traditional gap sizer is no longer accurate. When gap balancing, the amount of posterior resection is varied in order to achieve a flexion gap that matches a previously resected extension gap. For example, if the extension gap is relatively large, more posterior bone can be resected to increase the flexion gap in order to match the extension gap, and thus, a smaller femoral component can be utilized. Similarly, if the extension gap is relatively small, less posterior bone can be resected to decrease the flexion gap, and thus, a larger femoral component can be utilized. Traditional gap sizers require the surgeon to recognize this matching issue including determinative sizing repercussions and adjust the size of a femoral implant accordingly. This adds complexity and time to the procedure. Such balancing issues are addressed with the present tensioning instrument, which can measure the gap in both extension and flexion. This measurement can be made by a sensor that can provide such data to the computing device 104 or other electronic device for surgical planning, analysis and other purposes.

Figure 2:
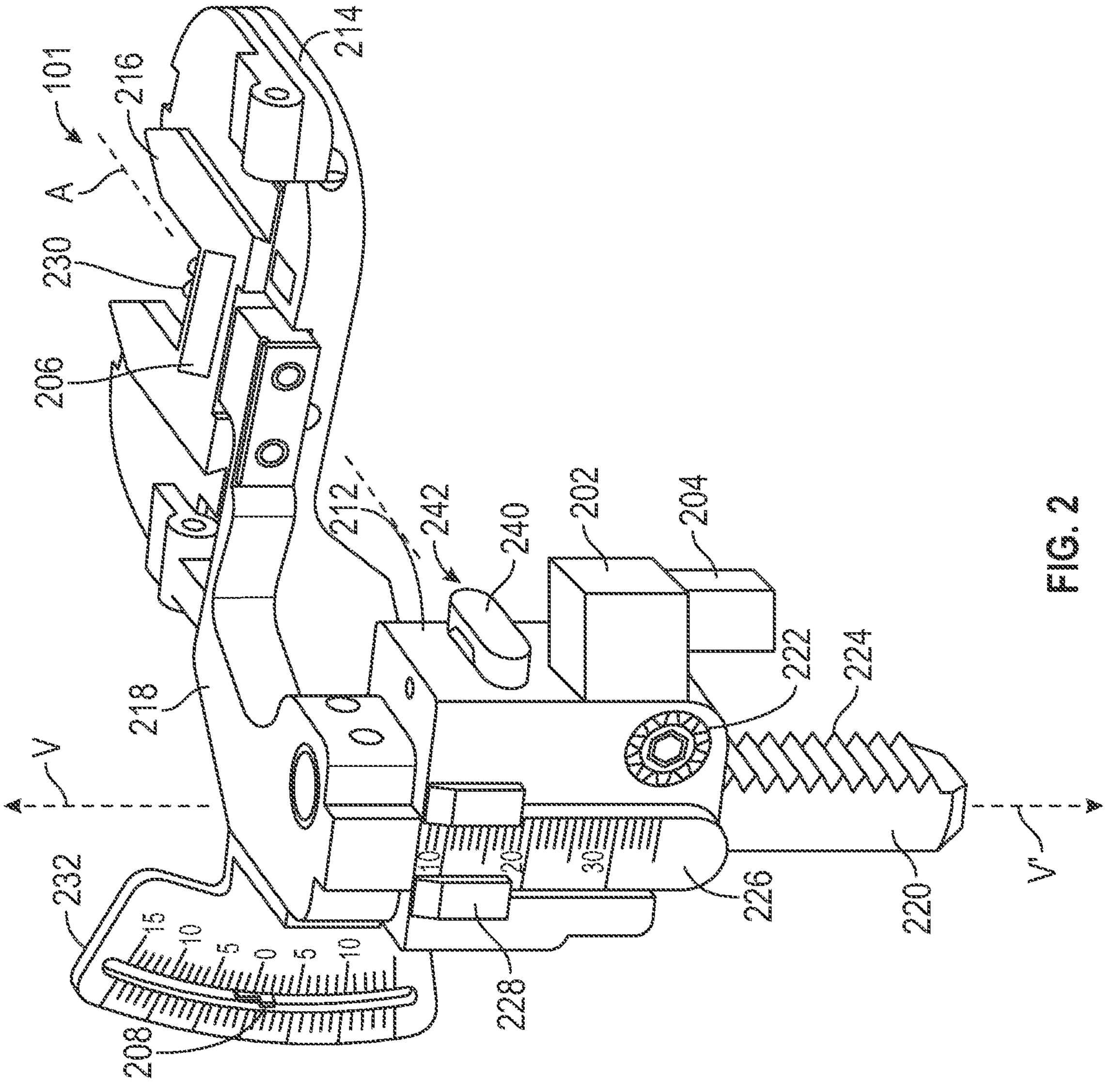
FIG. 2 is a perspective view of a knee joint tensioning instrument in accordance with an example of the present disclosure.

FIG. 2 shows an example of the tensioning instrument 101. This tensioning instrument 101 can be configured for separating a patient's tibia and femur and measuring tension, gap(s) and a joint angle(s) therebetween. The tensioning instrument 101 can include a first sensor 202, a second sensor 204, a third sensor 206, a fourth sensor 208, a base 212, a tibial component 214, a femoral component 216 and an intermediate arm 218 configured to couple the tibial component 214 to the femoral component 216. The tibial component 214 and femoral component 216 are illustratively offset from the base 212. The first sensor 202, the second sensor 204 and the fourth sensor 208 can be part of or can be otherwise be coupled to the base 212. The third sensor 206 can be part of, coupled to, or can be positioned above the femoral component 216.

The femoral component 216 can be configured to translate vertically along arrows V, V' relative to the tibial component 214 via the arm 218, as shown in FIG. 2. The tensioning instrument 101 can be opened by moving the femoral component 216 apart from the tibial component 214 along arrow V', and the tensioning instrument 101 can be closed by moving the femoral component 216 toward the tibial component 214 along arrow V. As shown in FIG. 2, the arm 218 can include the shaft 220 that translates vertically through the base 212. The femoral component 216 can be coupled to the arm 218 for movement therewith relative to the base 212. The shaft 220 can be keyed to the base 212 to permit vertical translation of the shaft 220 through the base 212 while preventing rotation of the shaft 220 in the base 212.

The femoral component 216 can be configured to engage with the femur of the patient. Similarly, the tibial component 214 can be configured to engage with the tibia of the patient. The femoral component 216 can be driven to separate the femur with respect to the tibia and the tibial component 214. In particular, a driving mechanism can be provided for selectively translating the femoral component 216 relative to the tibial component 214. In particular, a top portion of the driving mechanism can be coupled to the femoral component 216 via the arm 218, while the base 212, which is coupled to the tibial component 214 can ride independently thereof on the driving mechanism.

Figure 2A:
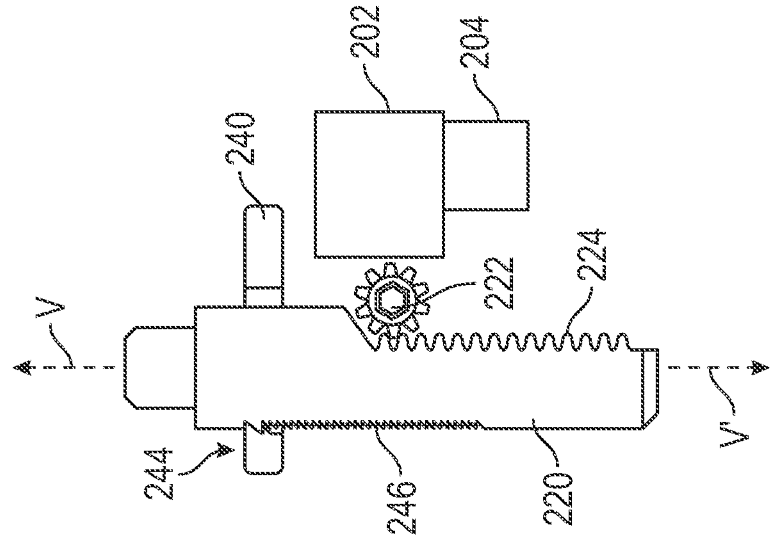
FIG. 2A is a plan view of parts of the tensioning instrument of FIG. 2A showing a rack, shaft, gear, a first sensor and a second sensor, in accordance with some embodiments.

The illustrative driving mechanism of FIGS. 2 and 2A can include a pinion gear 222 in base 212 that cooperates with a linear rack 224 on the shaft 220. In use, a hex driver or another suitable tool can be used to apply a torque to turn the gear 222, and the gear 222 meshes with the rack 224 to drive the rack 224 vertically along arrows V, V'. The tensioning instrument 101 is opened to apply a tension load to the patient's knee joint of about 40 lbs., about 60 lbs., about 80 lbs., or more, although the load may vary depending on sensed data, analytics and recommendation provided by the computing device 104, the surgeon's preference, the state of the patient's surrounding soft tissue, and/or other factors.

In some instances the driving mechanism may also act as a locking mechanism with the gear 222 meshing with the rack 224 in a manner that makes adjustment difficult to impossible without the hex driver or another suitable tool. Alternatively, a dedicated locking mechanism an also be incorporated in the tensioning instrument 101 to hold the femoral component 216 in place relative to the tibial component 214. The illustrative locking mechanism of FIGS. 2 and 2A can include a spring-biased lever 240 having an actuator end 242 and a pawl end (not shown in FIG. 2). The locking mechanism can allow tensioning instrument 101 to be freely opened, but can prevent the tensioning instrument 101 from being closed until the lever 240 is operated by the user. In some instances, the pawl (not shown) can permit vertically upward movement of femoral component 216 along arrow V when opening the tensioning instrument 101 but resists vertically downward movement of the femoral component 216 along arrow V' when closing the instrument 101. In some cases, when the actuator end 242 of the lever 240 is pressed inwardly by the user, the pawl (not shown) of the lever 240 can disengage from a ratchet or similar feature, thereby permitting vertically downward movement of the femoral component 216 to close the tensioning instrument 101. Other suitable locking mechanisms can include a detent mechanism or another suitable mechanical mechanism, for example.

As shown in FIGS. 2 and 2A, the first sensor 202 can be a torque sensor configured to measure torque on the gear 222, for example. For example, the torque sensor can be an assembly such as a Honeywell QWFK-8M miniature torque sensor. As discussed, the first sensor 202 can be housed or otherwise coupled in the base 212. The first sensor 202 can collect first data regarding the torque of the gear 222 when the tensioning instrument 101 is separating the tibia and the femur with the tibial component 214 and the femoral component 216, respectively. Such first data can be provided wirelessly or via wired connection to the computing device 104 of FIG. 1, for example.

Similarly, as shown in FIGS. 2 and 2A, the second sensor 204 can be configured as a position measuring device. The second sensor 204 can be configured to measure a distance or gap G (FIGS. 5 and 6) between the tibial component 214 and the femoral component 216 along arrows V, V'. The second sensor 204 can be an inductive sensor (e.g., microchip LX3301A) configured to detect presence of metal, in this case the shaft. Alternatively, the second sensor 204 can be an optical sensor such as a time of flight sensor or another type of sensor configured for position measurement. Such optical sensor could be configured to count the number of teeth of the rack, for example as a proxy for the position. In any case, the gap G (FIGS. 5 and 6) may be sensed by the second sensor 204, which can be configured to collect second data regarding a position of the femoral component relative to the tibial component when the tensioning instrument 101 is separating the tibia and the femur. The second data can be provided wirelessly or via wired connection to the computing device 104 of FIG. 1, for example.

Figure 5:
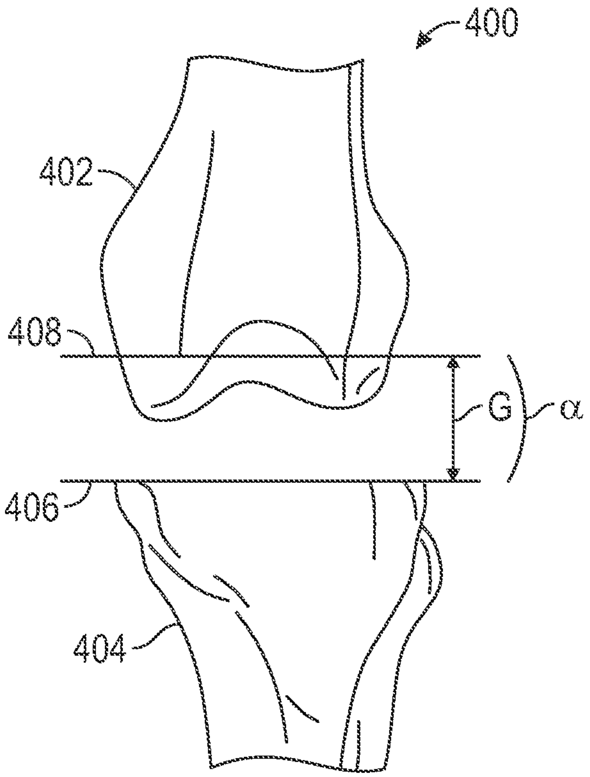
FIG. 5 is an anterior elevated view of a knee joint in extension in accordance with an example of the present disclosure.
Figure 6:
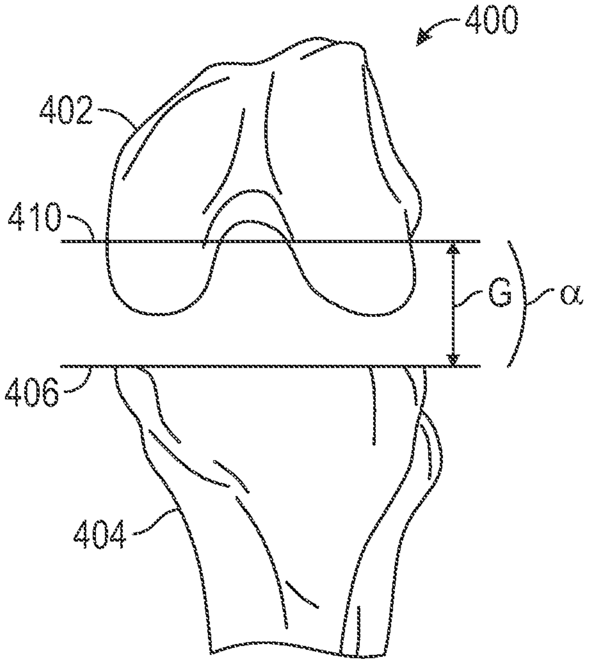
FIG. 6 is a is an anterior elevated view of the knee joint in flexion in accordance with an example of the present disclosure.

In addition to the ability of the femoral component 216 to translate vertically relative to the tibial component 214, the femoral component 216 can also be configured to rotate relative to the tibial component 214. More particularly, the femoral component 216 can also be configured to rotate relative to the arm 218 and the tibial component 214 about axis A of FIG. 2. As shown in FIG. 2, the post 230 can extend into the femoral component 216 from the arm 218 along the rotation axis A. The femoral component 216 can be configured to rotate around the post 30 and the rotation axis A. In some instances, the rotation axis A of the femoral component 216 can be substantially perpendicular to the translation axis defined along arrows V, V' of the femoral component 216. In FIG. 2, the fourth sensor 208 can be provided to measure the degree of rotation as rotation data. This rotation data can be provided wirelessly or via wired connection to the computing device 104 of FIG. 1, for example. The degree of rotation of the femoral component 216 relative to the tibial component 214 can correspond to an angle α (FIGS. 5 and 6). The angle α can be indicate a varus/valgus angle of the patient's knee joint and/or internal/external rotation of the patient's knee joint.

The third sensor 206 can be part of the femoral component 216 or can be placed above the proximal surface thereof. The third sensor 206 can be configured to measure directly a force or pressure of the femur counter-acting back against the tensioning instrument 101 when the tensioning instrument 101 is separating the femur from the tibia. In this manner, the third sensor 206 can measure the tensioning of the tensioning instrument 101 as applied to the knee joint. This data collected by the third sensor 206 can be provided to the wirelessly or via wired connection to the computing device 104 of FIG. 1, for example. However, measurement of such force using the third sensor 206 is optional and tension of the knee joint with the tensioning instrument can be derived from the torque collected as the first data of the first sensor 202.

Figure 3:
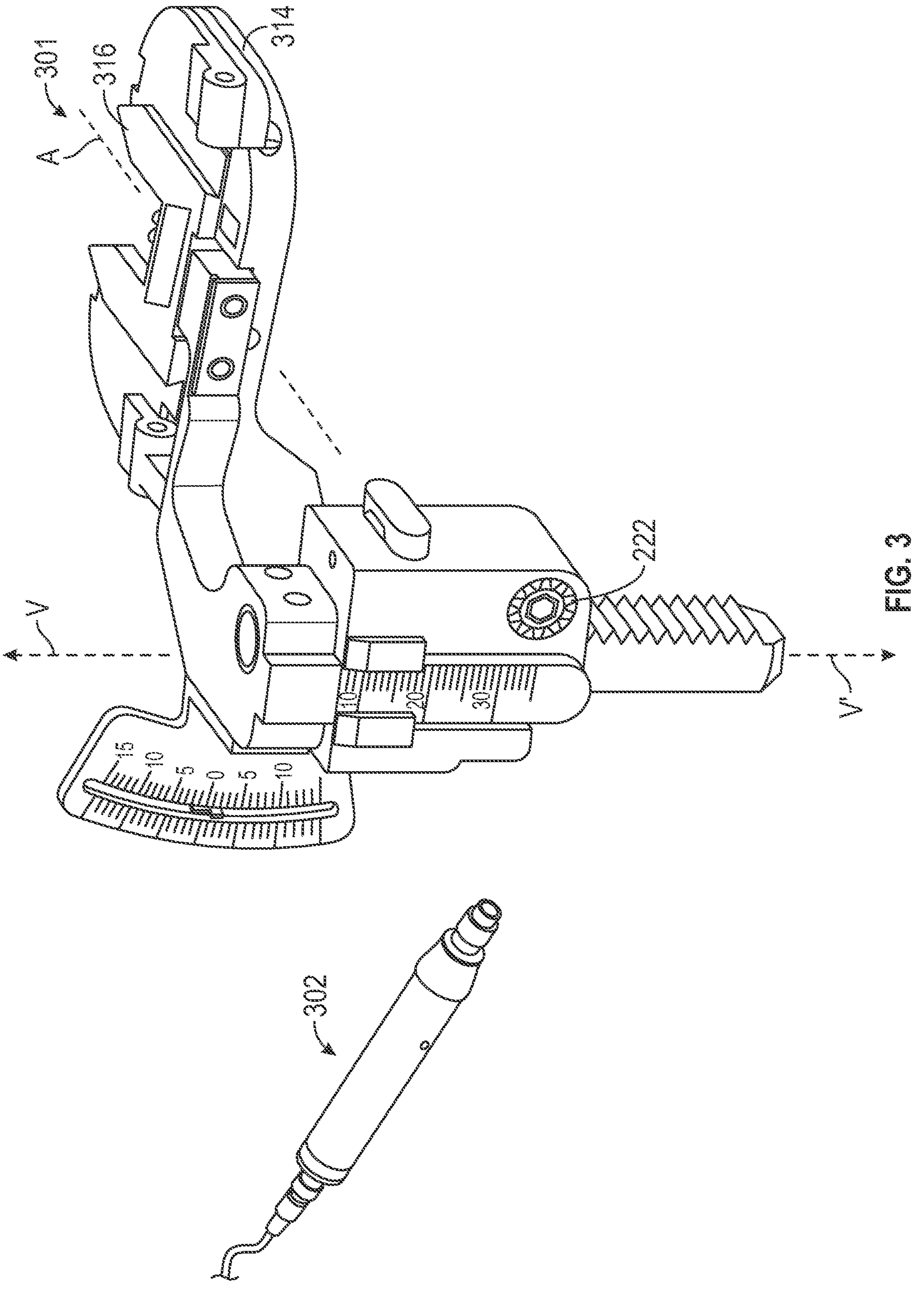
FIG. 3 is a perspective view of another example of a tensioning instrument and a first sensor that is part of a separate handheld torque screwdriver in accordance with one example of this disclosure.

FIG. 3 shows an tensioning instrument 301 that differs slightly from the tensioning instrument 101 of FIGS. 1-2A, in that the instrument 301 does not include the first sensor 202 (FIGS. 2 and 2A) as part of the instrument in the manner of the tensioning instrument 101 as a previously described. Rather, FIG. 3 illustrates a first sensor 302 that is part of a separate handheld torque screwdriver that is separate from but configured to couple with the tensioning instrument 301 (e.g., via coupling with the hex or other engagement feature that couples with the gear 222). The first sensor 302 can be an ng-TTH200-xi Handheld Torque Sensor manufactured by n*gineric of Villingen-Schwenningen, Germany for example. Thus, the first sensor 302 can be a torque sensor configured to measure torque applied to the gear 222, for example. The first sensor 302 can collect first data regarding the torque as applied to the gear 222 when the tensioning instrument 301 is separating the tibia and the femur with the tibial component 214 and the femoral component 216, respectively. Such first data can be provided wirelessly or via wired connection to the computing device 104 of FIG. 1, for example.

Figure 4:
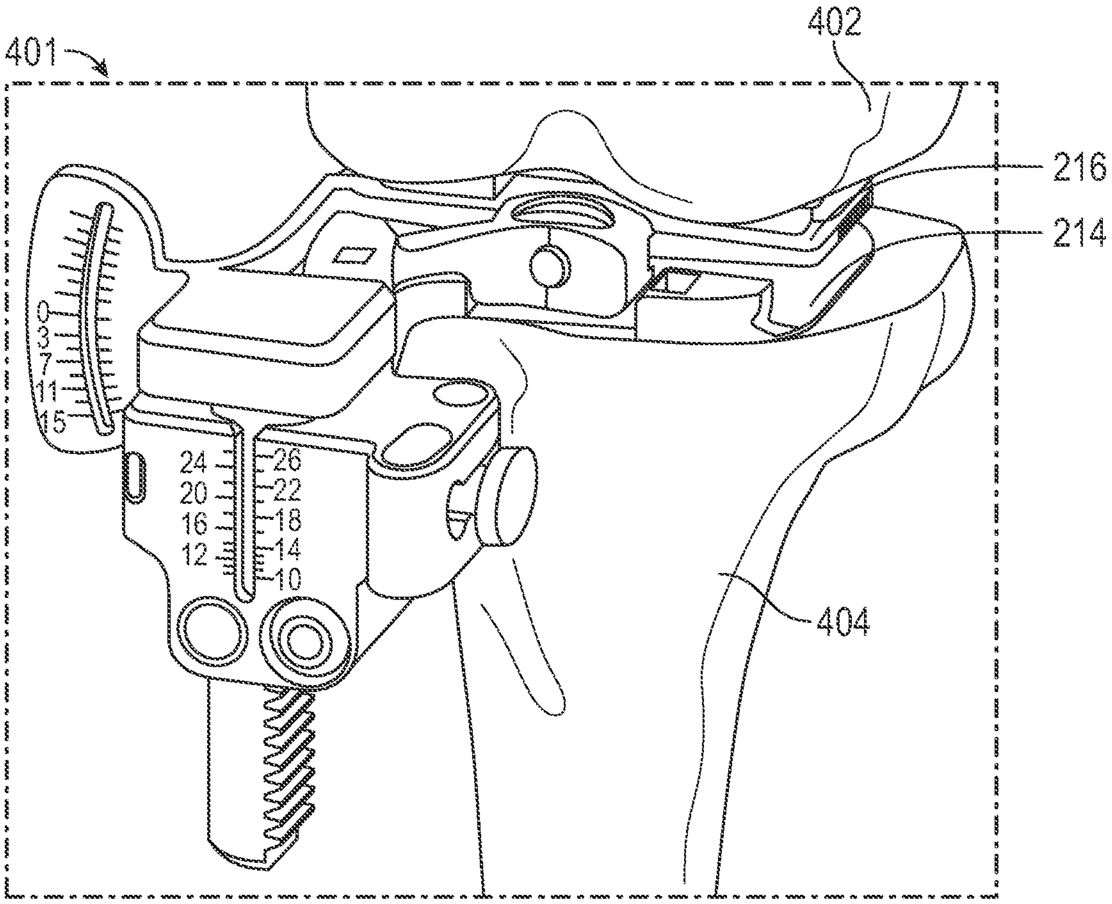
FIG. 4 shows yet another example of a tensioning instrument separating the femur from the tibia to place the knee joint in tension in accordance with one example of this disclosure.

FIG. 4 shows a tensioning instrument 401 similar to instruments 101 and 310 of FIGS. 1-3 acting to separate a femur 402 and a tibia 404. As with the other instruments 101 and 301, the tensioning instrument 301 includes the tibial component 214 configured for placement against the tibia and a femoral component 216 configured for placement against the femur. The femoral component 216 can be moveable relative to the tibial component 214 to place the knee joint in tension by separating the femur 402 and the tibia 404.

FIG. 5 knee joint 200 in extension as viewed from the anterior thereof. Similarly, FIG. 6 illustrates knee joint 200 in flexion as viewed from the anterior thereof. To obtain the views of FIGS. 5 and 6, a surgeon can expose the tibia 404 and femur 402 of the knee joint 400. This can involve pre-operative planning, incising the patient's skin, incising the patient's joint capsule, and removing osteophytes, for example.

The surgeon (or robotic surgical system) can use instrument 401 to separate tibia 404 and femur 402 of the patient's knee joint 400 to a desired tension, and to plan and identify the desired bone resections of the femur 402. This can be performed with advice/alerts/recommendation from the computing device 104 of FIG. 1, for example. With the patient's knee joint 200 tensioned in extension (FIG. 5), the surgeon with or without assistance can plan and identify a distal femoral resection 408 that will produce a desired gap G and angle α therebetween. As discussed previously, the extension angle α can be referred to as a varus/valgus angle in some instances. With the patient's knee joint 400 tensioned in flexion (FIG. 6), the user is able to plan and identify a posterior femoral resection 410 that will produce a desired gap G and angle α therebetween. The flexion angle α can be referred to as an internal/external rotation angle. Gap G and angle α between tibia 404 and femur 402 can be selected with analysis provided by the computing device 104 of FIG. 1 and can be based on the patient's age, patient's weight, patient's height, patient's knee state, the state of the patient's surrounding soft tissue (as measured quantitatively by one or more of the first, second, third and/or fourth sensors of FIG. 2, for example), the types or sizes of prosthetic implants being used, and other factors, for example.

The knee joint 400 can be prepared such that gap G and angle α between tibia 404 and femur 402 are the same or substantially the same in extension (FIG. 5) as in flexion (FIG. 6). For example, a three-dimensional space can be maintained between tibia 404 and femur 402 in extension and flexion, the size of this space can vary depending upon the anatomy of the patient. Thus, a surgeon implanting a prosthetic femoral implant having equally thick distal and femoral condyles can prepare an extension gap G that is the same as the flexion gap G, while a surgeon implanting a prosthetic femoral implant having distal and femoral condyles of different thicknesses can prepare an extension gap G that is not the exactly the same as the flexion gap G to account for the different thicknesses. When angle α is 0 degrees, such that the proximal tibial resection 406 is parallel to the distal femoral resection 408 in extension (FIG. 5) and the posterior femoral resection 410 in flexion (FIG. 6), the three-dimensional space between tibia 404 and femur 402 can be rectangular in shape in extension and flexion. It is also contemplated that the surgeon can tolerate differences between the extension angle α (FIG. 5) and the flexion angle α (FIG. 7), such as differences of a few degrees.

Figure 7:
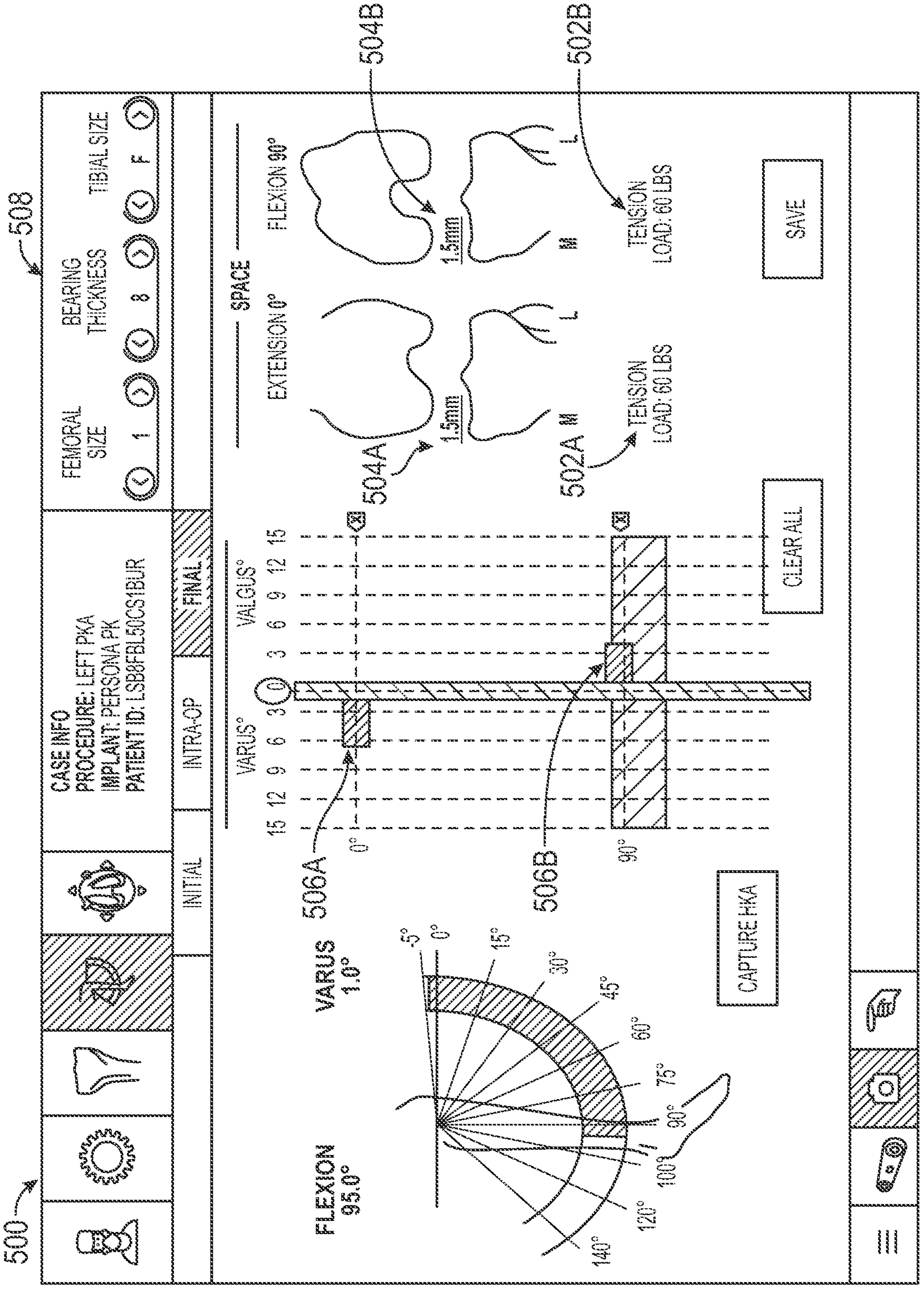
FIG. 7 is a diagram of a knee arthroplasty graphical user interface (GUI) in accordance with some embodiments.

FIG. 7 shows an example display 500 or other graphical user interface that can be used with the robotic surgical system 100 of FIG. 1. The display 500 can be updated and otherwise controlled by the computing device 104 of FIG. 1, for example. As shown in FIG. 7, the display 500 can include one or more indicators 502A and 502B of tension load of the tensioning instrument applied on the knee joint. The indicator 502A can be tension of the tensioning instrument with the knee joint in extension, while the indicator 502B can be tension of the tensioning instrument with the knee joint in flexion. As discussed, tension can be directly collected data (e.g., with third sensor) of corresponding force resisting tension or can be data collected and derived from the torque measured by the first sensor.

The display 500 can additionally include indicators 504A and 504B of a position of the femur relative to the tibia. This data can be collected by the second sensor of FIG. 2 as discussed previously. The indicator 504A can show the position of the femur (as approximated by the femoral component of the tensioning instrument) relative to the tibia (as approximated by the tibial component) with the knee in extension. The indicator 504B can be position of the femur (as approximated by the femoral component of the tensioning instrument) relative to the tibia (as approximated by the tibial component) with the knee in flexion.

The display can additionally include indicators 506A and 506B of the angle α between tibia and femur. This data can be collected by the fourth sensor of FIG. 2 as discussed previously. The indicator 506A can show the angle of the femur (as approximated by the femoral component of the tensioning instrument) relative to the tibia (as approximated by the tibial component) with the knee in extension. The indicator 506B can be the angle of the femur (as approximated by the femoral component of the tensioning instrument) relative to the tibia (as approximated by the tibial component) with the knee in flexion.

FIG. 7 also provides alert 508 to recommend implant sizes such as a femoral size, a bearing thickness and/or a tibial size. Such alerts and recommendation can be from predictive analytics using at least the first data and/or additional data (sensor, demographic, patient-specific, etc.) as discussed herein. Suggested settings for the tensioning device (e.g., torque, position, etc.) can also be provided on the display 500 according to further examples. Location of femoral resections can also be provided on the display 500. Location of femoral resections, implant size, etc. can be based upon predictive analytics using at least the first data and/or additional data (sensor, demographic, patient-specific, etc.) as discussed herein.

Figure 8:
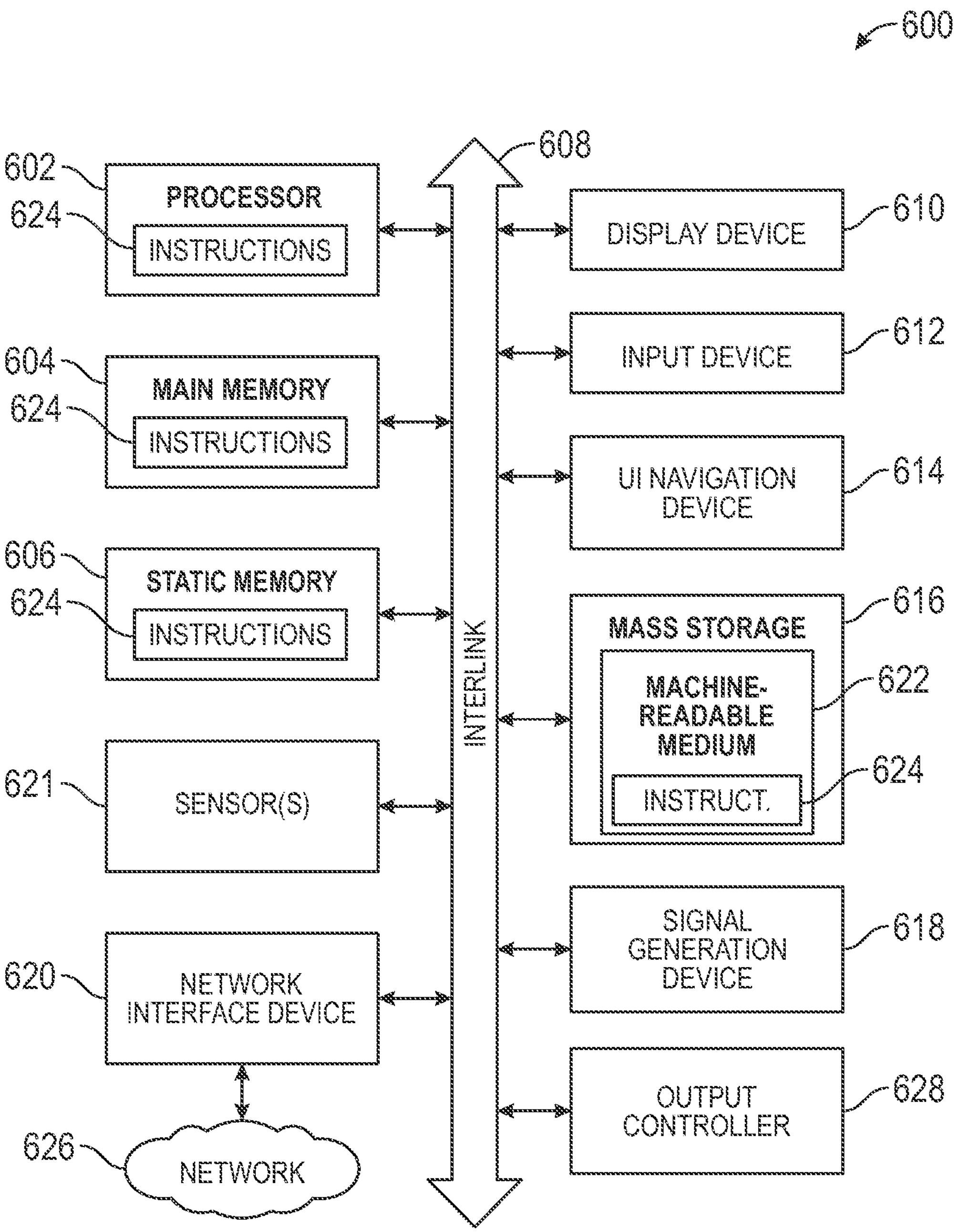
FIG. 8 illustrates an example of a block diagram of a machine upon which any one or more of the techniques (e.g., methodologies) discussed herein may perform in accordance with some embodiments.

FIG. 8 illustrates an example of a block diagram of a machine 600 upon which any one or more of the techniques (e.g., methodologies) discussed herein may perform in accordance with some embodiments. This machine can be the computing device 104 of FIG. 1, for example. In alternative embodiments, the machine 600 may operate as a standalone device or may be connected (e.g., networked) to other machines. In a networked deployment, the machine 600 may operate in the capacity of a server machine, a client machine, or both in server-client network environments. The machine 600 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610, an alphanumeric input device 612 (e.g., a keyboard), and a user interface (UI) navigation device 614 (e.g., a mouse). In an example, the display unit 610, alphanumeric input device 612 and UI navigation device 614 may be a touch screen display. The display unit 610 may include goggles, glasses, an augmented reality (AR) display, a virtual reality (VR) display, or another display component. For example, the display unit may be worn on a head of a user and may provide a heads-up-display to the user. The alphanumeric input device 612 may include a virtual keyboard (e.g., a keyboard displayed virtually in a VR or AR setting.

The machine 600 may additionally include a storage device (e.g., drive unit) 616, a signal generation device 618 (e.g., a speaker), a network interface device 620, and one or more sensors 621, such as a the one or more sensors described herein, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices.

The storage device 616 may include a machine readable medium 622 that is non-transitory on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 600, and includes digital or analog communications signals or other intangible medium to facilitate communication of such software.

Each of the following non-limiting examples (referred to as aspects and/or techniques below) may stand on its own, or may be combined in various permutations or combinations with one or more of the other examples:

In some aspects, the techniques described herein relate to a knee arthroplasty instrument for use in a knee joint, the knee joint including a tibia and a femur, the instrument optionally including: a tensioning instrument including a tibial component configured to engage the tibia and a femoral component configured to engage the femur, the femoral component being movably coupled to the tibial component to place the knee joint in tension by separating the tibia and the femur; and a first sensor coupled to the tensioning instrument and configured to collect first data regarding a torque of the tensioning instrument when separating the tibia and the femur.

In some aspects, the instrument further optionally including a second sensor coupled to the tensioning instrument and configured to collect second data regarding a position of the femoral component relative to the tibial component.

In some aspects, the first sensor is optionally coupled to a gear that meshes with a rack to drive movement of the femoral component.

In some aspects, the first sensor is optionally: a handheld torque screwdriver that couples with the gear or a torque sensor assembly mounted to the tensioning instrument.

In some aspects, the techniques described herein relate to a knee arthroplasty system optionally including: a tensioning instrument including a tibial component configured for placement against a tibia and a femoral component configured for placement against a femur, the femoral component being moveable relative to the tibial component to place a knee joint in tension by separating the tibia and the femur; a first sensor configured to collect first data regarding a torque of the tensioning instrument when separating the tibia and the femur; and a robotic surgical device including processing circuitry, the robotic surgical device configured to assist in the knee arthroplasty, wherein processing circuitry of the robotic surgical device electronically communicates with at least the first sensor to receive the first data and triggers an update of a display to visually indicate a tension load of the tensioning instrument based upon the torque.

In some aspects, the system further optionally including a second sensor configured to collect second data regarding a position of the femoral component relative to the tibial component, wherein the processing circuitry of the robotic surgical device electronically communicates with the second sensor to receive the second data and triggers an update of the display to visually indicate the position of the femoral component relative to the tibial component.

In some aspects, the processing circuitry optionally is configured to perform predictive analytics using at least the first data, wherein the processing circuitry is configured to output to the display a personalized recommendation for use of the tensioning instrument during the knee arthroplasty.

In some aspects, the personalized recommendation optionally includes one or more of: an alert to adjust the torque of the tensioning instrument, an alert to recommend a desired torque for the tensioning instrument prior to the separating the tibia and the femur with the tensioning instrument, an alert to adjust a distance between the femoral component and the tibial component, an alert to recommend a desired distance between the femoral component and the tibial component prior to the separating the tibia and the femur with the tensioning instrument, an alert recommending a size of a femoral implant or an alert recommending a position for a femoral resection of the femur.

In some aspects, the first sensor is optionally coupled to a gear that meshes with a rack to drive movement of the femoral component.

In some aspects, the first sensor is optionally: a handheld torque screwdriver that couples with the gear or a torque sensor assembly mounted to the tensioning instrument.

In some aspects, the techniques described herein relate to a method for intraoperatively determining a tension or laxity of a knee joint during a knee arthroplasty, the method optionally including: positioning a tensioning instrument within the knee joint, the tensioning instrument including a tibial component that abuts a tibia and a femoral component abuts a femur; tensioning the knee joint by separating the femur from the tibia with the tensioning instrument; measuring a torque of the tensioning instrument when separating the tibia and the femur; transmitting data regarding the torque to a robotic surgical device; and displaying a tension load of the tensioning instrument based upon the torque.

In some aspects, the method further optionally including: performing predictive analytics using at least the data regarding the torque to provide a personalized recommendation for use of the tensioning instrument during the knee arthroplasty; and adjusting the torque based upon the personalized recommendation.

In some aspects, the method further optionally including: measuring a position of the femur relative to the tibia when separated by the tensioning instrument; transmitting data regarding the position to the robotic surgical device; and displaying the position during the knee arthroplasty.

In some aspects, the method further optionally including: performing predictive analytics using at least the data regarding the torque and the data regarding the position to provide a personalized recommendation for use of the tensioning instrument during the knee arthroplasty; and adjusting at least one of the torque or position based upon the personalized recommendation.

In some aspects, the method further optionally including outputting control instructions to cause the robotic surgical device to perform the adjusting the at least one of the torque or position based upon the personalized recommendation.

In some aspects, the personalized recommendation is optionally provided prior to the tensioning of the knee joint with the tensioning instrument, and wherein the personalized recommendation includes a recommendation of a desired position for the femur relative to the tibia when separated by the tensioning instrument.

In some aspects, the personalized recommendation is optionally provided prior to the tensioning of the knee joint with the tensioning instrument, and wherein the personalized recommendation includes a recommendation of a desired torque for the tensioning instrument.

In some aspects, the measuring the torque of the tensioning instrument is optionally with a handheld torque screwdriver that engages the tensioning instrument.

In some aspects, the method further optionally including moving the knee joint through a range of motion with the tensioning instrument separating the tibia and the femur.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A knee arthroplasty system comprising:

a tensioning instrument including a tibial component configured for placement against a tibia and a femoral component configured for placement against a femur, the femoral component being moveable relative to the tibial component to place a knee joint in tension by separating the tibia and the femur, wherein the tensioning instrument includes comprises:

a base to which the tibial component and femoral component are coupled;

a gear at least partially housed inside the base, wherein the gear meshes with a rack to drive movement of the femoral component relative to the tibial component; and a first sensor at least partially housed inside the base and coupled to the gear of the tensioning instrument, the first sensor configured to collect first data regarding a torque of the tensioning instrument when separating the tibia and the femur; and a robotic surgical device including processing circuitry, the robotic surgical device configured to assist in a knee arthroplasty, wherein the processing circuitry of the robotic surgical device electronically communicates with at least the first sensor to receive the first data and triggers an update of a display to visually indicate a tension load of the tensioning instrument based upon the torque of the gear of the tensioning instrument.

2. The system of claim 1, further comprising a second sensor configured to collect second data regarding a position of the femoral component relative to the tibial component, wherein the processing circuitry of the robotic surgical device electronically communicates with the second sensor to receive the second data and triggers an update of the display to visually indicate the position of the femoral component relative to the tibial component.

3. The system of claim 1, wherein the processing circuitry is configured to perform predictive analytics using at least the first data, wherein the processing circuitry is configured to output to the display a personalized recommendation for use of the tensioning instrument during the knee arthroplasty.

4. The system of claim 3, wherein the personalized recommendation includes one or more of:

an alert to adjust the torque of the tensioning instrument, an alert to recommend a desired torque for the tensioning instrument prior to the separating the tibia and the femur with the tensioning instrument, an alert to adjust a distance between the femoral component and the tibial component, an alert to recommend a desired distance between the femoral component and the tibial component prior to the separating the tibia and the femur with the tensioning instrument, an alert recommending a size of a femoral implant or an alert recommending a position for a femoral resection of the femur.

5. A method for intraoperatively determining a tension or laxity of a knee joint during a knee arthroplasty, the method comprising:

positioning a tensioning instrument within the knee joint, the tensioning instrument including a tibial component that abuts a tibia and a femoral component abuts a femur, the tensioning instrument comprising:

a base to which the tibial component and femoral component are coupled;

a gear at least partially housed inside the base, wherein the gear meshes with a rack to drive movement of the femoral component relative to the tibial component; and a first sensor at least partially housed inside the base and coupled to the gear of the tensioning instrument, the first sensor configured to collect first data regarding a torque of the tensioning instrument when separating the tibia and the femur;

tensioning the knee joint by separating the femur from the tibia with the tensioning instrument;

measuring a torque of the tensioning instrument using the first sensor, the first sensor configured to collect first data regarding the torque of the tensioning instrument when separating the tibia and the femur;

transmitting data regarding the torque to a robotic surgical device including processing circuitry, the robotic surgical device configured to assist in a knee arthroplasty, wherein the processing circuitry of the robotic surgical device electronically communicates with at least the first sensor to receive the first data and triggers an update of a display; and displaying a tension load of the tensioning instrument based upon the torque of the gear of the tensioning instrument.

6. The method of claim 5, further comprising:

performing predictive analytics using at least the data regarding the torque to provide a personalized recommendation for use of the tensioning instrument during the knee arthroplasty; and adjusting the torque based upon the personalized recommendation.

7. The method of claim 6, wherein the personalized recommendation is provided prior to the tensioning of the knee joint with the tensioning instrument, and wherein the personalized recommendation comprises a recommendation of a desired torque for the tensioning instrument.

8. The method of claim 5, further comprising:

measuring a position of the femur relative to the tibia when separated by the tensioning instrument;

transmitting data regarding the position to the robotic surgical device; and displaying the position during the knee arthroplasty.

9. The method of claim 8, further comprising:

performing predictive analytics using at least the data regarding the torque and the data regarding the position to provide a personalized recommendation for use of the tensioning instrument during the knee arthroplasty; and adjusting at least one of the torque or position based upon the personalized recommendation.

10. The method of claim 9, further comprising outputting control instructions to cause the robotic surgical device to perform the adjusting the at least one of the torque or position based upon the personalized recommendation.

11. The method of claim 9, wherein the personalized recommendation is provided prior to the tensioning of the knee joint with the tensioning instrument, and wherein the personalized recommendation comprises a recommendation of a desired position for the femur relative to the tibia when separated by the tensioning instrument.

12. The method of claim 5, further comprising moving the knee joint through a range of motion with the tensioning instrument separating the tibia and the femur.

13. A knee arthroplasty system comprising:

a tensioning instrument including a tibial component configured for placement against a tibia and a femoral component configured for placement against a femur, the femoral component being moveable relative to the tibial component to place a knee joint in tension by separating a tibia and a femur of the knee joint, the tensioning instrument comprising:

a base to which the tibial component and femoral component are coupled;

a gear at least partially housed inside the base, wherein the gear meshes with a rack to drive movement of the femoral component relative to the tibial component; and a first sensor at least partially housed inside the base and coupled to the gear of the tensioning instrument, the first sensor configured to collect first data regarding a torque of the tensioning instrument when separating the tibia and the femur; and a robotic surgical device including processing circuitry, the robotic surgical device configured to assist in a knee arthroplasty, wherein the processing circuitry of the robotic surgical device is configured to:

(i) electronically communicate with at least the first sensor to receive the first data;

(ii) perform predictive analytics using at least the first data and a database of patient anatomical models to generate a personalized recommendation; and (iii) triggers an update of a display to visually indicate a tension load of the tensioning instrument based upon the torque and an alert recommending a position for a femoral resection of the femur based on the personalized recommendation.

14. The system of claim 13, further comprising a second sensor configured to collect second data regarding a position of the femoral component relative to the tibial component, wherein the processing circuitry of the robotic surgical device electronically communicates with the second sensor to receive the second data and triggers an update of the display to visually indicate the position of the femoral component relative to the tibial component.

15. The system of claim 13, wherein the personalized recommendation includes one or more of:

an alert to adjust the torque of the tensioning instrument, an alert to recommend a desired torque for the tensioning instrument prior to the separating the tibia and the femur with the tensioning instrument, an alert to adjust a distance between the femoral component and the tibial component, an alert to recommend a desired distance between the femoral component and the tibial component prior to the separating the tibia and the femur with the tensioning instrument, an alert recommending a size of a femoral implant or an alert recommending a position for a femoral resection of the femur.

* * * * *